United States Patent [19]

Elman

[11] Patent Number: 5,936,735
[45] Date of Patent: Aug. 10, 1999

[54] APPARATUS AND METHOD FOR DETERMINING THE OPTICAL RETARDATION OF A MATERIAL

[75] Inventor: James F. Elman, Fairport, N.Y.

[73] Assignee: Eastman Kodak Company, Rochester, N.Y.

[21] Appl. No.: 09/052,300

[22] Filed: Mar. 31, 1998

[51] Int. Cl.⁶ ........................................................ G01J 4/00
[52] U.S. Cl. ........................ 356/364; 356/369; 356/371
[58] Field of Search .................................... 356/364, 369, 356/371

[56]  References Cited

U.S. PATENT DOCUMENTS 4,893,932  1/1990  Knollenberg ........................ 356/237.5
4,909,630  3/1990  Gawrisch et al. .

FOREIGN PATENT DOCUMENTS 2338305  2/1975  Germany .

OTHER PUBLICATIONS

"Determination of Orientation in Thermotropic Liquid Crystalline Polymer Films by Spectrographic Measurement of the Birefringence" published in Macromolecules 1996, pp. 8726–8733.

FILMETRICS F20 "An Advanced Thin–Film Measurement System At A Breakthrough Price." published by FILMETRICS.

"Advanced Thin–Film Measurement Systems" published by FILMETRICS.

*Primary Examiner*—Frank G. Font
*Assistant Examiner*—Reginald A. Ratliff
*Attorney, Agent, or Firm*—Susan L. Parulski

[57]  ABSTRACT

An apparatus for determining the optical retardation of a material. The apparatus includes a light source emitting light along a light path, and a lens disposed in the light path intermediate the light source and a sample of the material. A waveguide directs the light from the light source to the sample and directs light reflected from the sample to a wavelength analyzer, whereby the wavelength analyzer detects the wavelengths of the reflected light. The apparatus of the present invention includes a sole polarizing element disposed in the light path intermediate the light source and the wavelength analyzer.

14 Claims, 3 Drawing Sheets

APPARATUS AND METHOD FOR DETERMINING THE OPTICAL RETARDATION OF A MATERIAL

FIELD OF THE INVENTION

The present invention relates generally to optical characteristics of materials, and more particularly, to an apparatus and method for determining the optical retardation of optically anisotropic materials.

BACKGROUND OF THE INVENTION

Anisotropic materials have unequal physical properties along different axes. Optically anisotropic materials are typically birefringent. That is, light waves are split upon entry into the anisotropic material into two waves with differing velocities and hence different refractive indices. An example of an optically anisotropic material is a polymeric film such as polyester.

An optical characteristic of an anisotropic material is optical retardation. Optical retardation is defined as the product of thickness and birefringence. More particularly:

$$R = t * \text{birefringence} \qquad \text{Equation 1}$$

Written alternatively, $$R = t * (n_1 - n_2) \qquad \text{Equation 2}$$

wherein:
t is thickness,
$n_1$ is the index of refraction in a first direction, and
$n_2$ is the index of refraction in a second direction perpendicular to the first direction.

Apparatus and methods exist for determining the birefringence of a material. For example, German Patent No. DE 23 38 305 C3 (Frangen) discloses a method for determining the linear birefringence of a material, particularly in a form suitable for use in process control. Using transmission, Frangen teaches a first polarizer upstream of the material, and a second polarizer downstream of the material whose plane of polarization is perpendicular to that of the first polarizer. A photoelectrical receiving unit downstream of the second polarizer detects the wavelengths to determine birefringence. A separate thickness measuring device is provided.

A reference titled, "Determination of Orientation in Thermotropic Liquid Crystalline Polymer Films for Spectrographic Measurement of the Birefringence", by Beekmans and de Boer, *Macromolecules*, Vol 29, No. 27, American Chemical Society, 1996, teaches a transmission apparatus suitable for determining birefringence. FIG. 1 illustrates the optical setup for spectrographic birefringence measurements. A light source 10 directs light through a lens 12 and a first polarizer 14 onto sample 16. The light is transmitted through sample 16 and second polarizer 18, and impinges a diode array 20 of a detector 22. The wavelengths of the light impinging diode array 20 are analyzed by a computer 24.

An apparatus for measuring thickness and the index of refraction is commercially available from FILMETRICS of San Diego, Calif. FILMETRICS' product F20 determines film thickness and wavelength-dependent optical constants by acquiring reflectivity values at 512 wavelengths. Product literature identifies the performance specifications for a sample thickness range of 10 nm to 50 µm. Referring to FIG. 2, light from light source 20 is directed along a fiber optic cable 26 and through a lens 28 onto sample 16. The light is reflected back through fiber optic cable 26 into a spectrometer 30 where the reflected light is analyzed.

It may be desirable to determine only retardation, and not the specific values of thickness and/or birefringence. Therefore, while the German apparatus and the Beekmans and deBoer apparatus may have achieved a certain level of success, they afford a complex solution for Applicant's particular application. The FILMETRICS apparatus also does not provide an apparatus and method for determining retardation directly.

As such, a need continues to exist for an apparatus and method for determining retardation directly, that is, without determining the specific values of thickness and birefringence. A suitable apparatus is preferably simple in design, transportable, and compact in size. A suitable method is robust, consistent, and provides analysis results quickly.

SUMMARY OF THE INVENTION

An object of the present invention is to provide an apparatus and method for determining retardation directly.

Another object of the invention is to provide such an apparatus that is simple in design and transportable.

Still another object of the invention is to provide such a method that is robust and consistent.

These objects are given only by way of illustrative example. Thus, other desirable objectives and advantages inherently achieved by the disclosed invention may occur or become apparent to those skilled in the art. The invention is defined by the appended claims.

According to one aspect of the invention, there is provided an apparatus for determining the optical retardation of a material. The apparatus includes a light source emitting light along a light path, and a lens disposed in the light path intermediate the light source and a sample of the material. A waveguide directs the light from the light source to the sample and directs light reflected from the sample to a wavelength analyzer, whereby the wavelength analyzer detects the wavelengths of the reflected light. The apparatus of the present invention includes a sole polarizing element disposed in the light path intermediate the light source and the wavelength analyzer.

The present invention provides an apparatus and method for determining retardation without determining the specific values of thickness and birefringence. The apparatus is simple in design, transportable, and compact in size, while the method is robust, consistent, and provides analysis results quickly.

BRIEF DESCRIPTION OF THE DRAWINGS

The foregoing and other objects, features, and advantages of the invention will be apparent from the following more particular description of the preferred embodiments of the invention, as illustrated in the accompanying drawings.

DETAILED DESCRIPTION OF THE INVENTION

Figure 1:
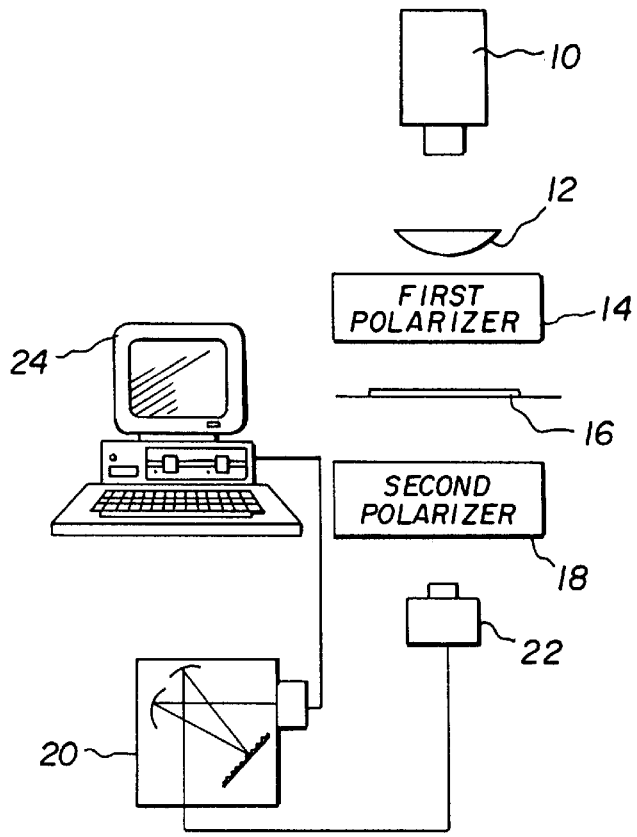
FIG. 1 shows a prior art transmission apparatus for determining birefringence.
Figure 2:
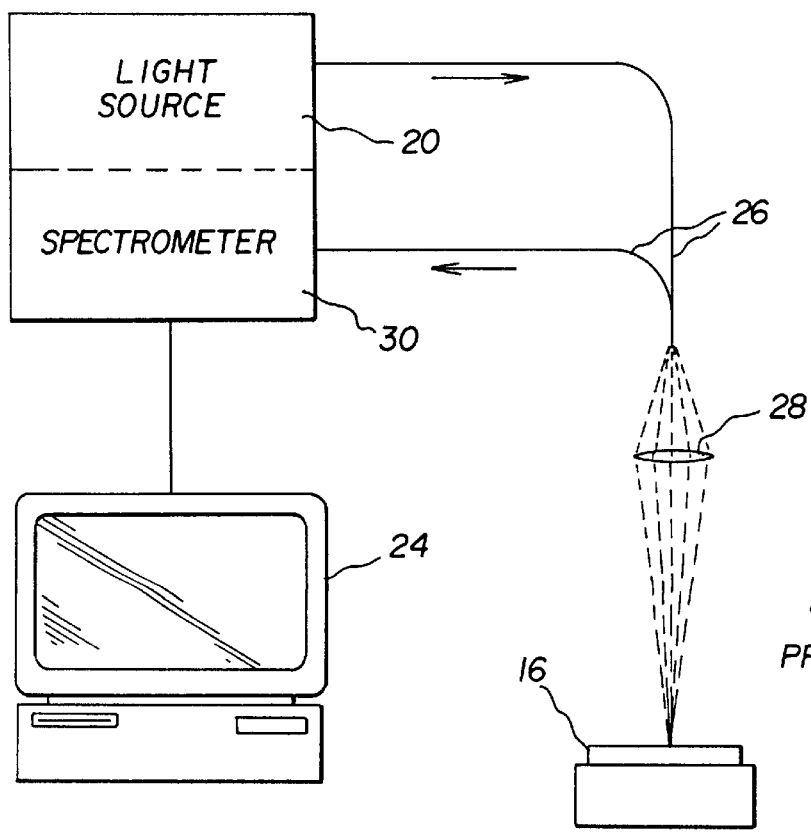
FIG. 2 shows a prior art reflection apparatus for determining thickness.

The following is a detailed description of the preferred embodiments of the invention, reference being made to the drawings in which the same reference numerals identify the same elements of structure in each of the several figures.

Figure 3:
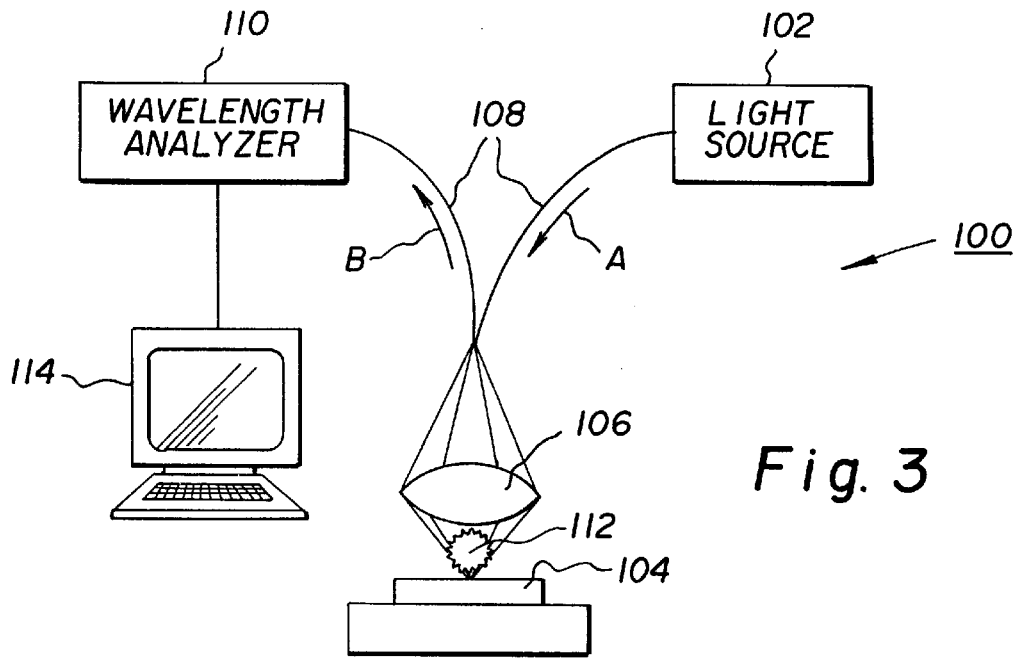
FIG. 3 shows a first embodiment of an apparatus for determining retardation in accordance with the present invention.

A first embodiment of an apparatus in accordance with the present invention is shown in FIG. 3. Optical retardation determination unit 100 includes a light source 102 emitting light along a light path toward a sample 104 of a material. A lens 106 is disposed in the light path intermediate light source 102 and sample 104. A waveguide 108 may be employed to direct the light along the light path. For the embodiment illustrated in FIG. 3, waveguide 108 is preferably a bifurcated fiber optic cable. Waveguide 108 directs light from light source 102 in a direction shown by arrow A. The light is reflected by sample 104, and the reflected light is directed toward a wavelength analyzer 110 by waveguide 108 in a direction shown by arrow B. A sole polarizing element 112 is disposed in the light path, intermediate light source 102 and wavelength analyzer 110. As illustrated, polarizing element 112 is more particularly disposed intermediate sample 104 and lens 106.

Polarizing element 112 can be any polarizing element known to those skilled in the art, including low quality polarizing elements, beamsplitters and mirrors. While polarizing element 112 is preferably disposed at 45 degrees relative to sample 104, operation is suitable in other geometries. Polarizing element 112 should not be disposed approximately or exactly parallel to sample 104.

Wavelength analyzer 110 is adapted to detect the wavelength of the reflected light. A spectrometer is an example of wavelength analyzer 110. A computer 114 is in electrical connection with wavelength analyzer 110 to manipulate the data from wavelength analyzer 110 to determine the optical retardation of sample 104.

Figure 4A:
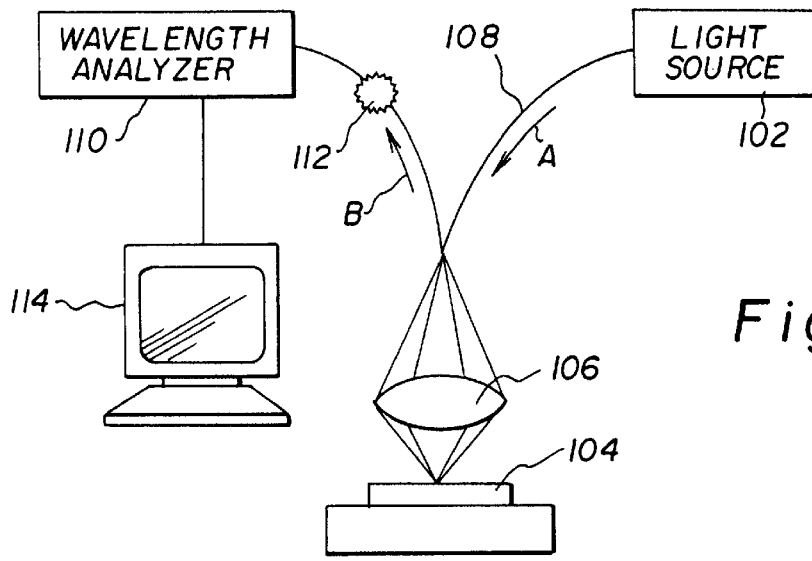
FIGS. 4(*a*) through 4(*c*) show alternative embodiments of the apparatus of FIG. 3.
Figure 4B:
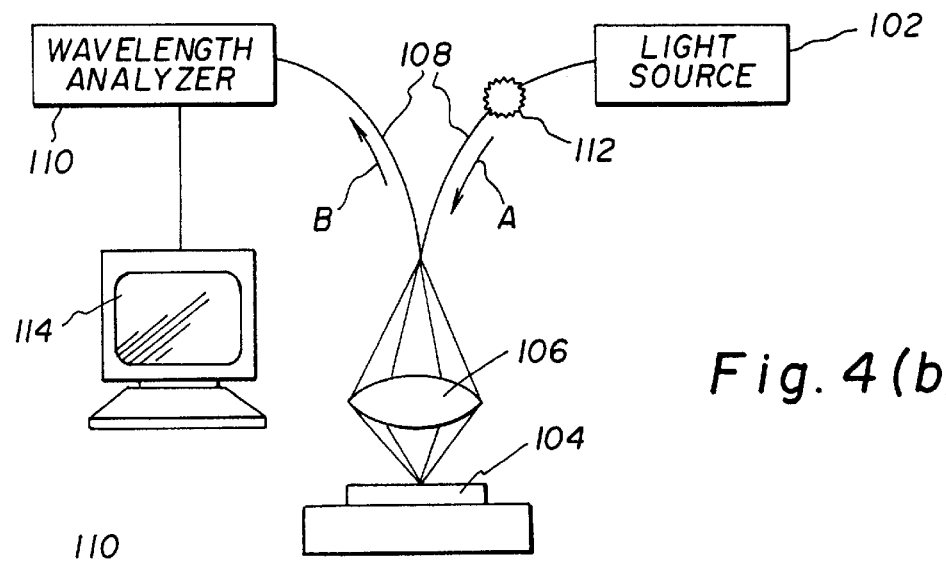
Figure 4C:
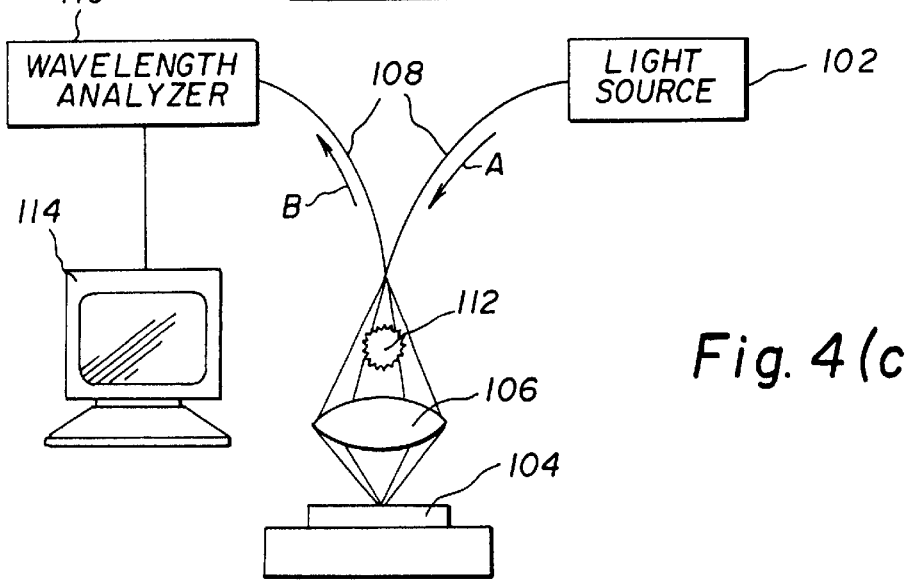

Referring now to FIGS. 4(a) through 4(c), the single polarizing element may be disposed alternatively within the optical retardation measuring unit. FIG. 4(a) illustrates an embodiment wherein polarizing element 112 is disposed intermediate lens 106 and wavelength analyzer 110. FIG. 4(b) illustrates another embodiment wherein polarizing element 112 is disposed intermediate light source 102 and lens 106. FIG. 4(c) further illustrates an embodiment wherein polarizing element 112 is also disposed intermediate light source 102 and lens 106, adjacent lens 106.

For the embodiments illustrated in FIGS. 4(a) and 4(b), if waveguide 108 is a fiber optic cable, then a polarizing-maintaining fiber optic cable must be employed to maintain the polarization of the reflected light. The embodiments of FIGS. 3 and 4(c) do not require polarizing-maintaining fiber optic cable; the beam of light is twice polarized due to the positioning of the polarizing element.

Referring again to FIG. 3, in operation, a beam of light is directed by light source 102 along waveguide 108 toward sample 104. Prior to being reflected from sample 104, the light beam is directed through lens 106 and polarized by being transmitted through polarizing element 112. The polarized light is reflected from sample 104 and directed back through polarizing element 112 and lens 106, toward wavelength analyzer 110 by waveguide 108.

A wavelength analyzer 110, such as a spectrometer, includes a diffraction grating (not shown) and a photodiode array (not shown) having a plurality of pixels responsive to a predetermined wavelength. The reflected light is directed onto the diffraction grating to provide discrete wavelengths. The discrete wavelengths are impinged onto a photodiode of the photodiode array where the pixels of the photodiode array indicate the wavelength of the light. The discrete wavelengths of the light are analyzed to determine intensity.

Figure 5:
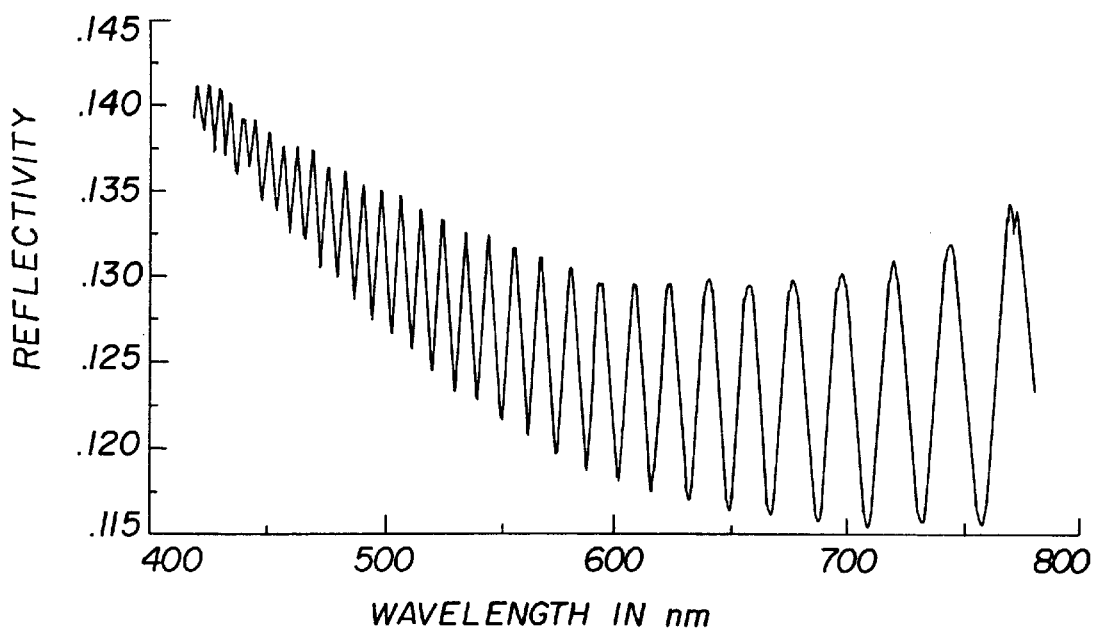
FIG. 5 shows a plot of wavelength versus reflection.

FIG. 5 illustrates a graph of the wavelength versus reflection data that would be provided by wavelength analyzer 110.

The data obtained in the graph of FIG. 5 is analyzed to obtain retardation. The retardation analysis of the discrete wavelengths of FIG. 5 can be accomplished using techniques known to those skilled in the art. One technique is described in German Patent No. DE 23 38 305 C3 (Frangen), referenced above. Generally described, Frangen identifies the maxima and minima wavelengths of the discrete peaks. The method described by Frangen is incorporated herewith by reference. This technique is suitable for the embodiments illustrated in FIGS. 3 and 4(a) through 4(c). Other retardation analysis methods may be known by those skilled in the art.

The retardation analysis provides a single numerical value for the graph of FIG. 5. This single value is the retardation value R, as noted in Equation 1 or Equation 2.

As is apparent from the description of the present invention, an apparatus and method is provided for determining retardation without determining the specific values of thickness and birefringence. The apparatus is simple in design, transportable, and compact in size, while the method is robust, consistent, and provides analysis results quickly. A feature of the present invention is the reduced number of optical elements. A further feature of the present invention is the enhanced range. That is, for a given retardation, reflection provides twice the number of fringes as transmission, the apparatus of the present invention is able of measuring half the retardation as that of a transmissive apparatus. For example, if a transmissive apparatus has a retardation range of 5 $\mu$m to 200 $\mu$m, the present invention has a retardation range of 2.5 $\mu$m 100 $\mu$m. Still further, the apparatus of the present invention lends itself to the inclusion of a microscope for the measurement of retardation on a micro scale.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An apparatus for determining the optical retardation of a material, comprising:

a light source emitting light along a light path;

a lens disposed in the light path intermediate the light source and a sample of the material;

a wavelength analyzer;

a waveguide directing the light from the light source to the sample and directing light reflected from the sample to the wavelength analyzer, the wavelength analyzer adapted to detect the wavelengths of the reflected light; and a sole polarizing element disposed in the light path intermediate the light source and the wavelength analyzer.

2. The apparatus according to claim 1 wherein the sole polarizing element is disposed intermediate the light source and the lens.

3. The apparatus according to claim 1 wherein the sole polarizing element is disposed intermediate the lens and the sample.

4. The apparatus according to claim 1 wherein the sole polarizing element is disposed intermediate the lens and the wavelength analyzer.

5. The apparatus according to claim 1 wherein the waveguide is a bifurcated fiber optic cable.

6. The apparatus according to claim 5 wherein the bifurcated fiber optic cable is a polarizing-maintaining fiber optic cable.

7. A method for determining a numeric value of the optical retardation of a material, comprising the steps of:

directing a beam of light toward a sample of the material;

directing the beam of light through a lens;

polarizing the beam of light;

reflecting the beam of light from the sample;

directing the reflected beam of light toward a wavelength analyzer; and analyzing the reflected beam of light to determine the numeric value of the optical retardation of the sample.

8. The method according to claim 7 wherein the step of polarizing the beam of light is accomplished prior to reflecting the beam of light from the sample.

9. The method according to claim 7 wherein the step of polarizing the beam of light is accomplished subsequent to reflecting the beam of light from the sample.

10. The method according to claim 7 wherein the step of analyzing the reflected beam is accomplished by:

directing the reflected beam onto a diffraction grating to provide discrete wavelengths, impinging the discrete wavelengths onto a photodiode having a plurality of pixels responsive to a predetermined wavelength, analyzing the discrete wavelengths to determine an intensity of the wavelengths of the reflected beam, and generating the numeric value of the optical retardation of the sample.

11. A method for determining the optical retardation of a material, comprising the steps of:

directing a beam of light toward a sample of the material;

directing the beam of light through a lens;

polarizing the beam of light;

reflecting the beam of light from the sample;

directing the reflected beam of light toward a wavelength analyzer;

directing the reflected beam onto a diffraction grating to provide discrete wavelengths;

impinging the discrete wavelengths onto a photodiode having a plurality of pixels responsive to a predetermined wavelength; and analyzing the discrete wavelengths to determine a numeric value of the optical retardation of the sample.

12. The method according to claim 11 wherein the step of polarizing the beam of light is accomplished prior to reflecting the beam of light from the sample.

13. The method according to claim 11 wherein the step of polarizing the beam of light is accomplished subsequent to reflecting the beam of light from the sample.

14. An apparatus for determining a numeric value of the optical retardation of a material, comprising:

a light source emitting light along a light path;

a lens disposed in the light path intermediate the light source and a sample of the material;

a wavelength analyzer adapted to detect the relative intensities of the constituent colors of the light directed thereon;

a waveguide directing the light from the light source to the sample and directing light reflected from the sample to the wavelength analyzer; and a sole polarizing element disposed in the light path intermediate the light source and the wavelength analyzer.

* * * * *